(12) United States Patent
Gomez (10) Patent No.: US 10,709,626 B1
(45) Date of Patent: Jul. 14, 2020

(54) APPARATUS FOR SECURING A PATIENT IN THE TRENDELENBURG POSITION DURING SURGERY

(71) Applicant: David J. Gomez, Holly Springs, NC (US)

(72) Inventor: David J. Gomez, Holly Springs, NC (US)

( * ) Notice: Subject to any disclaimer, the term of this patent is extended or adjusted under 35 U.S.C. 154(b) by 340 days.

(21) Appl. No.: 15/437,017

(22) Filed: Feb. 20, 2017

Related U.S. Application Data (60) Provisional application No. 62/296,863, filed on Feb. 18, 2016, provisional application No. 62/409,578, filed on Oct. 18, 2016.

(51) Int. Cl.
*A61G 7/10* (2006.01)
*A61G 13/12* (2006.01)

(52) U.S. Cl.
CPC ......... *A61G 7/1023* (2013.01); *A61G 7/1026* (2013.01); *A61G 7/1073* (2013.01); *A61G 13/1295* (2013.01); *A61G 2210/90* (2013.01)

(58) Field of Classification Search
CPC ............... A61G 13/126; A61G 13/122; A61G 13/1225; A61G 13/123; A61G 7/1026
See application file for complete search history.

(56) References Cited

U.S. PATENT DOCUMENTS

| | | | | |
|---|---|---|---|---|
| 3,452,372 A * | 7/1969 | Emery | ............... | A47C 1/146 297/377 |
| 3,829,914 A * | 8/1974 | Treat | ............... | A47C 21/00 5/495 |
| 5,787,523 A * | 8/1998 | Lindberg | ............... | A47G 9/0238 5/81.1 HS |
| 6,874,176 B2 * | 4/2005 | Berge | ............... | A61G 7/05707 5/627 |
| 9,021,640 B2 * | 5/2015 | Mohr | ............... | A61G 7/05738 5/740 |
| 9,024,107 B1 * | 5/2015 | Pero | ............... | A61F 13/47 604/358 |
| 2004/0172763 A1 * | 9/2004 | Sachs | ............... | A47C 3/16 5/656 |
| 2005/0055768 A1 * | 3/2005 | Assink | ............... | A61G 1/01 5/81.1 R |
| 2005/0241067 A1 * | 11/2005 | Nichols | ............... | B32B 27/12 5/420 |
| 2007/0056096 A1 * | 3/2007 | Assink | ............... | A47C 27/14 5/81.1 HS |
| 2013/0152950 A1 * | 6/2013 | Giap | ............... | A61F 5/3776 128/872 |
| 2013/0180046 A1 * | 7/2013 | Davis, Jr. | ............... | A61G 7/1026 5/81.1 HS |

(Continued)

*Primary Examiner* — Peter M. Cuomo
*Assistant Examiner* — Ifeolu A Adeboyejo
(74) *Attorney, Agent, or Firm* — Phillips Lytle LLP; David L. Principe (57) ABSTRACT

The apparatus of the present invention provides an apparatus for moving a patient on a pad and holding the pad in place on the surgical table. The disposable pad works in conjunction with the reusable patient lifting/moving base, allowing nurses to more readily and easily move patients on the table in order to facilitate surgical positioning. In another embodiment, the entire apparatus may be disposable. A pressure sensitive adhesive may hold the pad in place and prevent slippage between the pad and the top of the surgical table.

8 Claims, 7 Drawing Sheets

(56) References Cited

U.S. PATENT DOCUMENTS

| | | | |
|---|---|---|---|
| 2014/0143956 A1* | 5/2014 | Mohr | A61G 7/05738 5/740 |
| 2015/0143628 A1* | 5/2015 | Fowler | A61G 7/001 5/81.1 T |
| 2016/0100690 A1* | 4/2016 | Winkelman | B68G 5/02 297/250.1 |
| 2016/0279007 A1* | 9/2016 | Flatt | A61G 13/126 |
| 2017/0348173 A1* | 12/2017 | Bennetts | A61G 13/1285 |

* cited by examiner

APPARATUS FOR SECURING A PATIENT IN THE TRENDELENBURG POSITION DURING SURGERY

CROSS-REFERENCE TO RELATED APPLICATION

The present invention claims priority benefit of U.S. Provisional Patent Application No. 62/296,863 filed on Feb. 18, 2016, entitled "Method and Apparatus for Securing a Patient in the Trendelenburg Position During Surgery" and U.S. Provisional Patent Application No. 62/409,578 filed on Oct. 18, 2016, entitled "Method and Apparatus for Securing a Patient in the Trendelenburg Position During Surgery," both of which are hereby incorporated by reference.

TECHNICAL FIELD

The present invention relates generally to the field of medical devices for use in the surgical theater, and more particularly to an apparatus for securing a patient in the Trendelenburg position and a method of using such an apparatus to move patients more ergonomically to facilitate a surgical procedure.

BACKGROUND ART

Current pad systems such as the "Pigazzi Pad" disclosed in U.S. Pat. No. 8,464,720 B1; the Ocean Breeze Pad by Prime Medical; and many other similar pads offered in the surgical market space; rely on either securing a viscoelastic pad via the bed rail system by means of hook and loop fastener based systems, or using the pad's viscoelastic surface along with the patient's weight to keep the pad from sliding. These systems are designed to keep the pad and the patient from sliding during surgical bed positioning changes, most commonly the Trendelenburg (head down) surgical position. This angled Trendelenburg position may range from 0 to 40 degrees. As with current viscoelastic pad systems, standard draw sheets (both woven and nonwoven materials) are then placed under the patient to either move the patient or to keep the patient's arms in place at the patient's side. It is important to note that these draw sheets can minimize full contact surface between the patient's back (skin) and the pad or gel surface increasing the risk or possibility for patient slippage or drifting in gravity dependent positions. This result is due to a reduction in contact between the viscoelastic pad and the patient's skin resulting in less friction or impression/residual compression needed to keep the patient in a static position. These risks are compounded with each increase in the angle of the Trendelenburg position.

One problem with existing pad or gel based systems is that once they are secured to bed rails, the existing systems are not easily moveable, especially when under the weight of the patient. They are fixed in their location once secured. This limits ease of movement of the patient to an optimal surgical position once the patient is settled into the pad system and secured. Due to the lack of easy and ergonomic movement of patients placed upon these fixed surfaces, providers are routinely forced to place the patient in a less than optimal position for anesthesia airway access needed for direct laryngoscopy, a necessary requirement for general anesthesia. Providers either place short patients more proximal to them for optimal airway access, or place patients farther down the table away from them, to minimize the repetitive lifting of patients under general anesthesia.

Because most pads are fixed and secured via hook and loop fastener straps, providers must physically and bodily lift the patient off of the semi adhesive pad/gel systems in order to move the patient into the correct bed position required for surgery. In the disclosure of the Pigazzi patent (U.S. Pat. No. 8,464,720 B1) this is performed via the "cloth-like" draw sheet, which is also used to facilitate arm adduction. The draw sheet included in many viscoelastic foam packs is made of a paper/cloth like material and often lacks full strength to facilitate movement of the patient by providers when positioning changes are required. The providers must routinely grab bodily portions of the patient's torso in contact with the pad in order to move the patient down. It is fairly common in practice to see the pad move or bundle under the patient as larger patients cannot be fully elevated off of the pad thereby dragging the pad with the patient. This foam or gel bundling can lead to pressure points that may lead to injury (e.g., pressure-related skin injuries).

Routine movement and methodologies for moving patients on these pad/gel based systems begin to fail, especially during the care of moderate to morbidly obese patients. Rising obesity rates in the United States also place significant ergonomic safety and injury risks to health care providers as they must routinely physically lift and move these patients in order to facilitate certain surgical procedures. The healthcare industry faces a problem with a lack of products focused on improving methodologies and practices that facilitate less variance and safe care strategies, i.e., process improvements required for surgical positioning. The industry also lacks products designed to provide safer and more ergonomic processes for moving patients, which can be a key contributor to musculoskeletal disorders (MSD) and injuries (especially involving the back) suffered by providers.

BRIEF SUMMARY OF THE INVENTION

The apparatus of the present invention improves and optimizes clinical efficacy, time, staff utilization, and safety for both patients and staff. The pad system facilitates standardization of care by creating less variance during use, while serving to improve safety for providers during ergonomic weight bearing physical movements routinely required during surgical positioning.

The apparatus of the present invention provides a standard approach to moving patients during routine and well known surgical procedures requiring positioning changes while securing the patient by means of a unique material reinforced viscoelastic pad using a non-residue pressure sensitive adhesive ("PSA") system. The apparatus improves the standard viscoelastic/gel-based pads because it does not require hook and loop fasteners to secure the pad in place, improving the utility of the system over current designs and applications for use.

The apparatus of the present invention reduces or eliminates the need to pick the patient off of a viscoelastic/gel-based pad via either the "draw sheet" or awkward manual bodily lifting methodologies conducted by the staff.

Instead, the apparatus of the present invention provides a fully moveable system that moves both pad and patient and even helps transfer the patient to a post-operative stretcher, which also aids ergonomic processes inherent in surgical care.

DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 1:
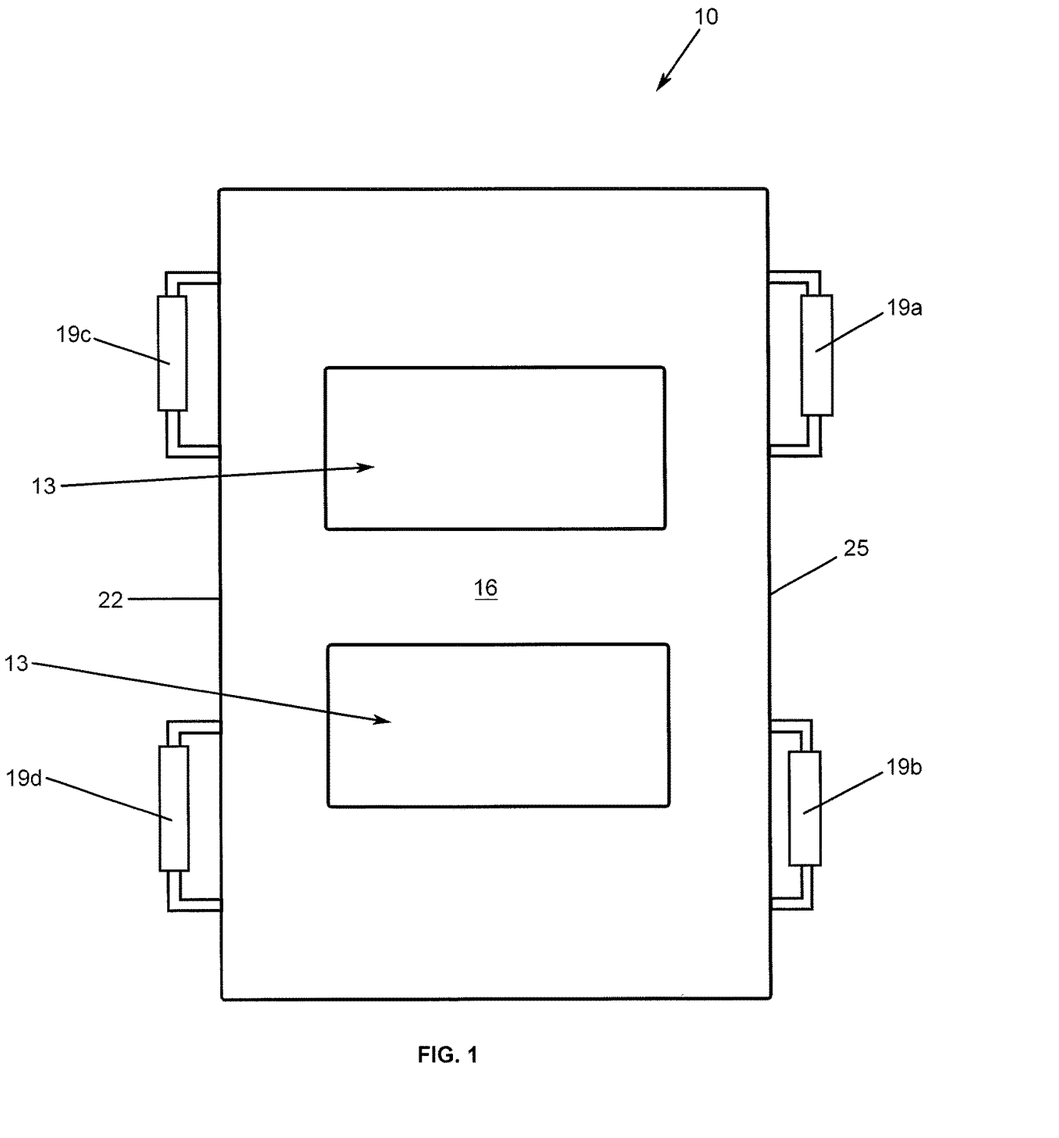
FIG. 1 is a top plan view of the base of the apparatus of the present invention.
Figure 2:
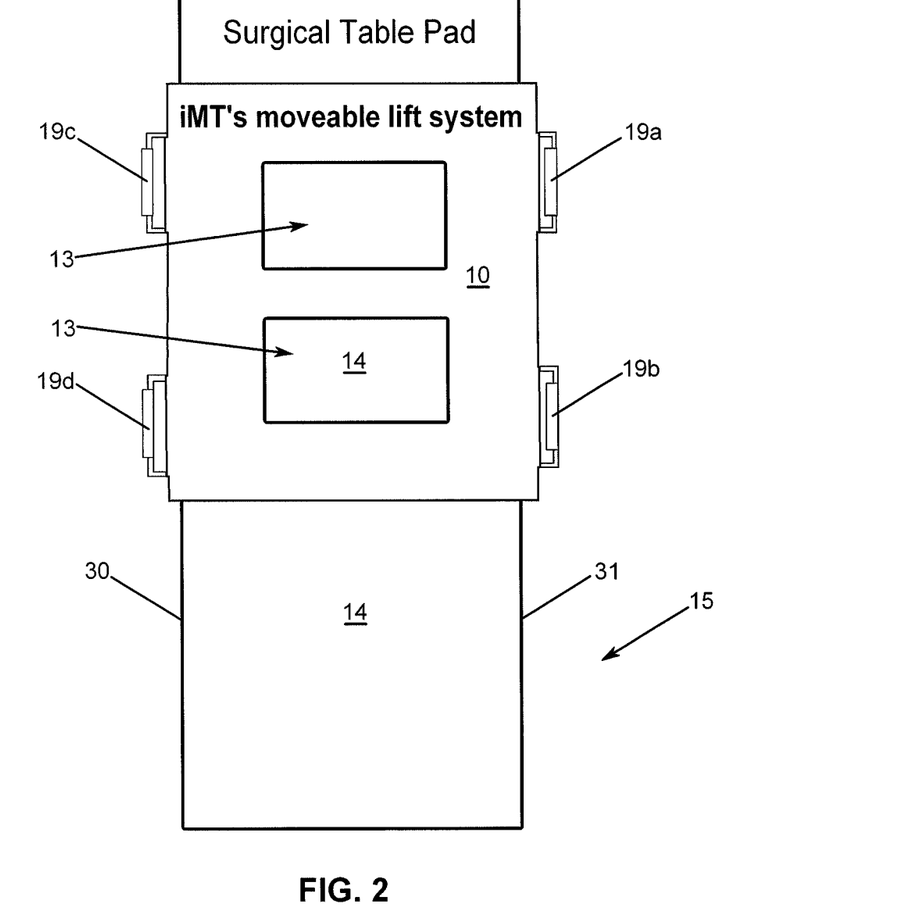
FIG. 2 is a top plan view of the base supported on a surgical table.

Referring now to the drawings, and more particularly to FIG. 1 thereof, this invention provides a base 10 made of a flexible material. The base 10 may be provided with a least one opening 13 in a central portion 16. The opening 13 exposes the top surface 14 of the surgical table 15 or surgical mattress through the base 10 (FIG. 2). The base 10 is also provided with a plurality of handles 19a, 19b, 19c, and 19d disposed along the sides 22, 25 of the base 10. The handles 19a-d may be formed by loops of material attached to the sides 22, 25 of the base 10. The handles 19a-d are sized to receive the hand of a provider such that the provider can grasp the handles 19a-d with their hands in order to move the base 10 along the length of the surgical table 15 to position and re-position the patient as necessary during a surgical procedure.

Turning to FIG. 2, the base 10 is shown in position relative to a surgical table 15. As shown the handle portions 19a-d of the base 10 extend along the sides 30, 31 of the surgical table 15 and are in a position to be grasped by a provider standing next to the surgical table 15. In this manner, a provider positioned on each side of the surgical table 15 can move the patient easily in either direction along the surgical table 15 by grabbing the handles 19a-d and lifting the patient with the cooperation of a provider standing on the opposite side. Alternatively, two providers on each side can each grab a handle 19a-d to move heavier patients.

Figure 3:
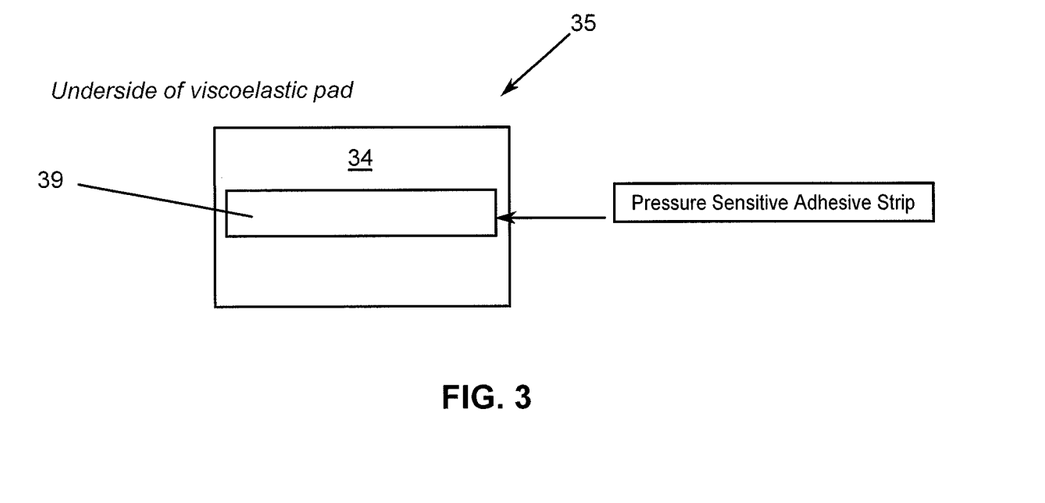
FIG. 3 is a bottom plan view of the viscoelastic pad of the present invention.

In FIG. 3, the underside 34 of a viscoelastic pad 35 is shown. The underside 34 has a pressure sensitive adhesive strip 39 disposed thereon. The pressure sensitive adhesive strip 39 may be provided with a protective cover (not shown) that is removed prior to use. The cover is removed from the pressure sensitive adhesive strip 39 and then the pad 35 is placed over the base 10 such that the pressure sensitive adhesive strip 39 aligns with the openings 13 in the base 10. The pressure sensitive adhesive strip 39 makes contact with the top surface 14 of the surgical table 15 through the openings 13 in the base 10. As a result, the pad 35 is held in position on the surgical table 15 by means of the pressure sensitive adhesive strip 39. The adhesive strip 39 prevents the pad 35 and base 10 from sliding relative to the surgical table 15, but can be removed for repositioning the pad 35 on the surgical table 15. When the pressure sensitive adhesive strip 39 on the bottom 34 of the pad 35 is lifted off of the surgical table 15, the adhesive strip 39 does not leave any residue on the surface of the surgical table 15.

Figure 4:
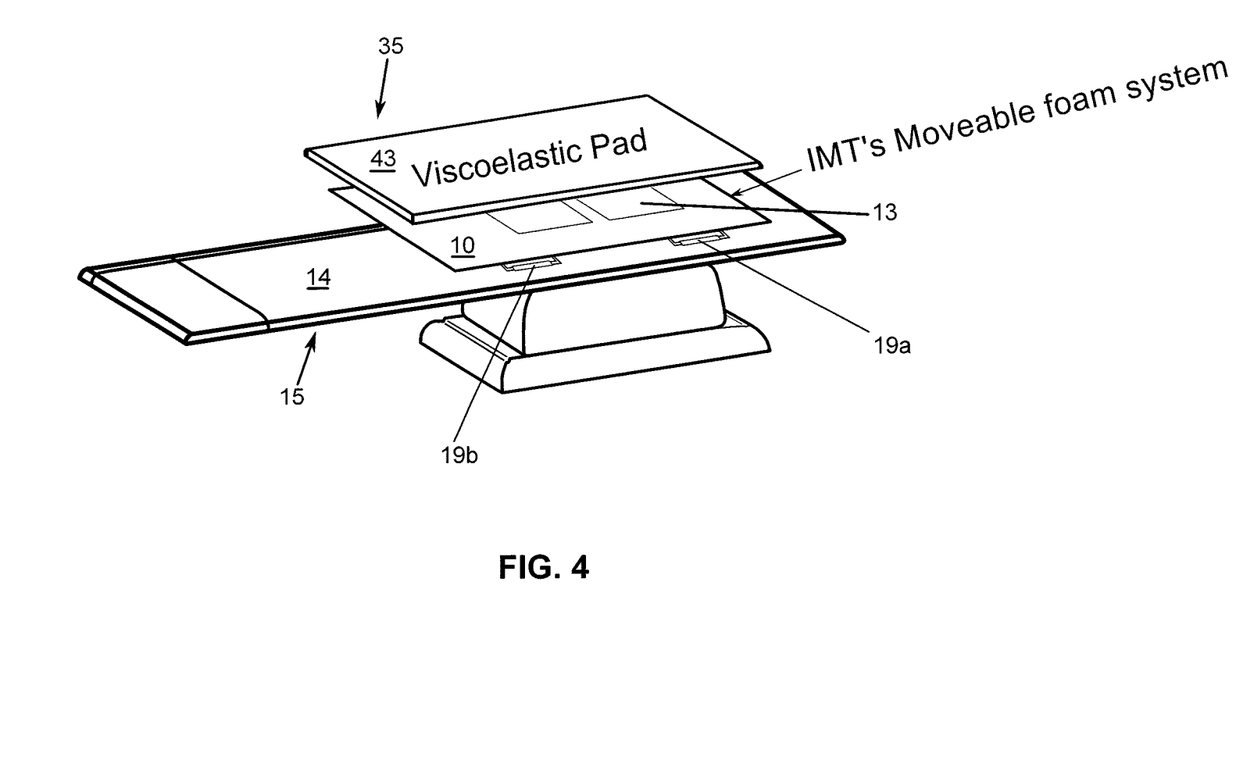
FIG. 4 is an exploded perspective view of the base and viscoelastic pad of the present invention in position on the surgical table.

In FIG. 4, the apparatus of the present invention is shown. The base 10 is placed directly onto the surgical table 15 and can be repositioned by means of the handles 19a-d extending from the sides 22, 25 of the base 10. The viscoelastic pad 35 having a re-positionable pressure sensitive adhesive strip 39 on a bottom surface 34 (FIG. 3) is placed on top of the base 10 such that the pressure sensitive adhesive strip 39 aligns with the openings 13 in the base 10. Next, the patient is placed on the top surface 43 of the viscoelastic pad 35.

It is very common for patients to be routinely moved after anesthesia induction and laryngoscopy (endotracheal tube placement), to another position on the surgical table (pad or gel) in order to facilitate surgical care. More routinely is the need to move the patient in a range of two to twelve inches distally towards the foot of the bed to facilitate positions like lithotomy. It is also very common for anesthesia providers to request the patient at the head of the surgical table, proximal to the provider. This is a safety concern as securing of the airway is one of the most important aspects of anesthesia care. In patients of moderate to morbid obesity, it is important to facilitate this approximation to the provider for many clinical and safety reasons.

The very nature of the padding used in standard surgical practice is to reduce potential for pressure related injuries to skin, muscle and more importantly nerves. This is the nature of padding in the perioperative setting. The apparatus of the present invention supports the notion of optimizing safety for the patient and the staff through its multiple and cumulative utility applications. Understanding routine processes of care in relation to how patients are positioned within the operating room along with staff methodologies is key to understanding the intent of the present design and its use within the perioperative setting.

The apparatus of the present invention provides an approach to moving patients during routine and well known surgical procedures requiring positioning changes while securing them via a unique material (nonwoven and durable re-usable) reinforced viscoelastic pad using a non-residue pressure sensitive adhesive. This apparatus is an improvement over the standard viscoelastic/gel-based pads as it requires no hook and loop fastener based straps to secure the apparatus in place, thereby improving the modularity and utility of existing pad designs in order to facilitate safer patient movement methodologies and processes required for surgical care. The apparatus of the present invention reduces the need to pick the patient off a viscoelastic/gel-based pad via either "draw sheet" or awkward manual movements conducted by staff, providing for a fully moveable system that moves both the pad and the patient.

The apparatus of the present invention provides an improved disposable, nonwoven fused viscoelastic pad with a pressure sensitive adhesive for holding the pad in place on the surgical table in place of hook and loop fastener straps attached to the bed rail. The disposable foam pad works in conjunction with the reusable patient lifting/moving non durable material base, allowing nurses to more readily and easily move patients on the table in order to facilitate surgical positioning. The pressure sensitive adhesive holds the pad in place and prevents slippage between the pad and the top of the surgical table. Furthermore, the pressure sensitive adhesive will not leave an adhesive residue which provides for better cleaning and decontamination. Historically, it is known that adhesive residue is a haven for opportunistic infectious pathogens within the clinical setting. Many pathogens reside in residue, potentially leading to hospital acquired infections (HAI's) and/or surgical site infections (SSI's).

The viscoelastic pad of the present invention will remain in contact with the surgical mattress through its durable material base, yet allows for movement of the entire apparatus when used to move a patient. The pressure sensitive adhesive on the bottom of the pad releases contact when the patient is lifted via the straps on the base and then resettles and reattaches to the surgical mattress when the patient is moved to their final surgical table position which keeps the entire apparatus in place during gravity dependent surgical table positions commonly used during surgery. This is not possible with current systems that require hook and loop fastener based straps. There is also not enough support structure to allow standard viscoelastic pads to lift and move patients. The ergonomic handles 19a-d on the base 10 improve and optimize ergonomic methods for providers during patient repositioning and improve the efficiency and efficacy of handling the patient.

Figure 5:
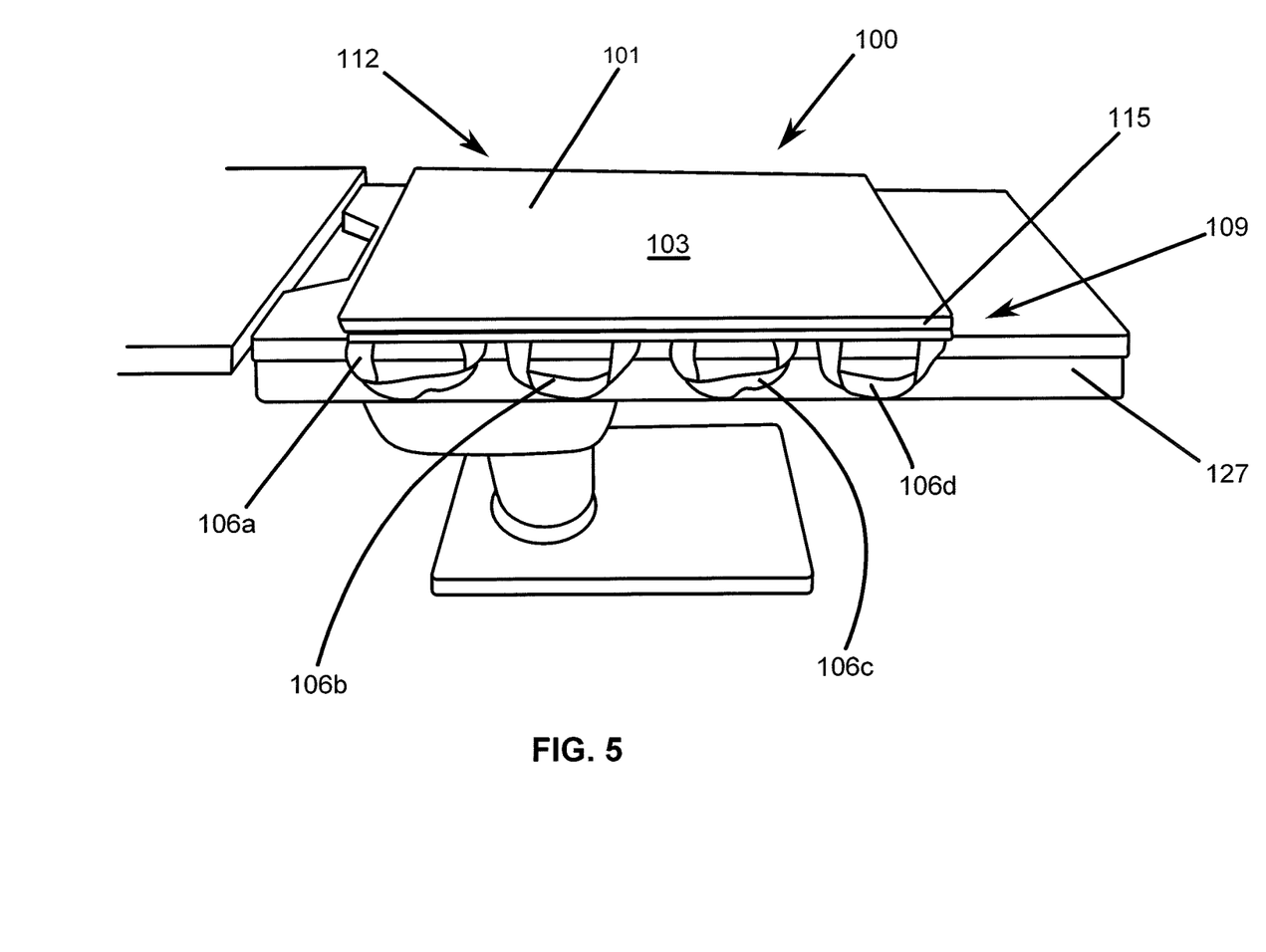
FIG. 5 is a top perspective view of an alternate embodiment of the invention showing a pad assembly supported on a surgical table.
Figure 6:
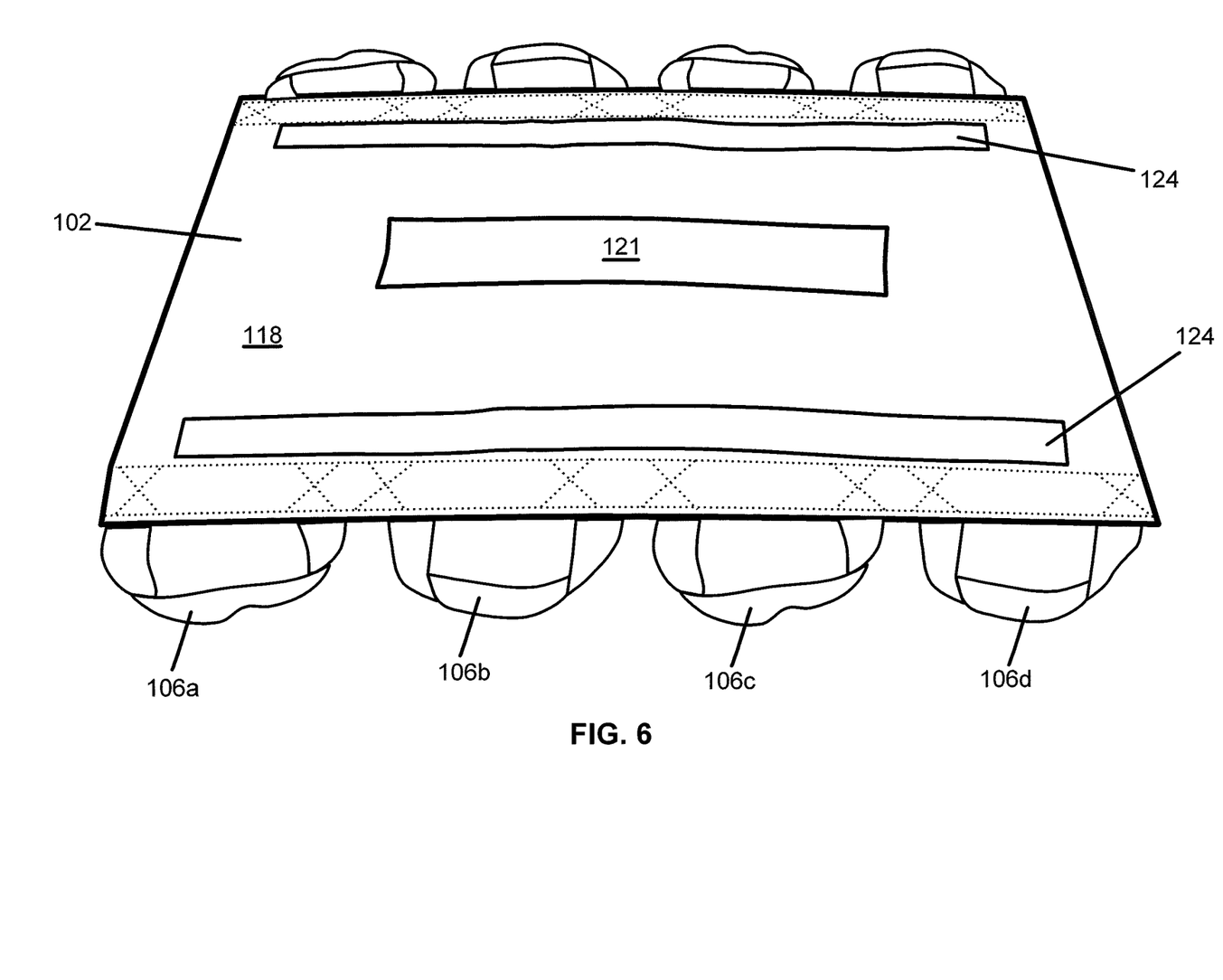
FIG. 6 is a bottom perspective view of the pad assembly shown in FIG. 5.

Turning to FIG. 5 in another embodiment of the invention, a disposable pad assembly 100 may be formed by fusing a standard use viscoelastic pad 101 to a nonwoven layered material 102 (FIG. 6) such as SMS (spun-melt-spun) or similar celluloid material. The pad assembly 100 may be provided with multiple handles 106a-d along opposed outside edges 109, 112 to provide grabbing points for lifting the pad assembly 100 and the patient (not shown) during use. In use, the patient is positioned on surface 103. The pad assembly 100 may also include one or more additional reinforcement layers 115 constructed of a condensed foam or biodegradable cardboard piece (placed between the nonwoven layers of the pad assembly 100). This reinforced pad assembly structure 115 keeps the whole pad assembly 100 from bunching up under the patient when lifting and/or repositioning the patient. It also allows the provider to pull back in case the patient was not positioned correctly. This adjustment is to facilitate distal perineal placement of the patient distally toward the surgical field. Currently the patients have to be repeatedly moved toward the distal end of the pad to keep the perineal space open for surgery. The nonwoven is separated from the pad at this end, allowing the nonwoven to be folded under thereby improving perineal placement. A warming support structure inlay may be placed between nonwoven materials in place of the foam or cardboard support structure 115. This warming support structure allows the transfer of heat to the patient from under the pad system, reinforcing the foams natural ability to be both insulator and conductor of heat. The bottom surface 118 (FIG. 6) of the pad assembly 100 may be provided with an anti-skid rubber foam strip 121 and/or a pressure sensitive adhesive (PSA) strip 124. This pad assembly 100 allows patients to be lifted evenly as weight is distributed through the semi-rigid support structure 115 under the viscoelastic pad 101. After use, the entire pad assembly 100 may be discarded. In FIG. 5, the pad assembly 100 is shown supported by a surgical table 127.

Figure 7:
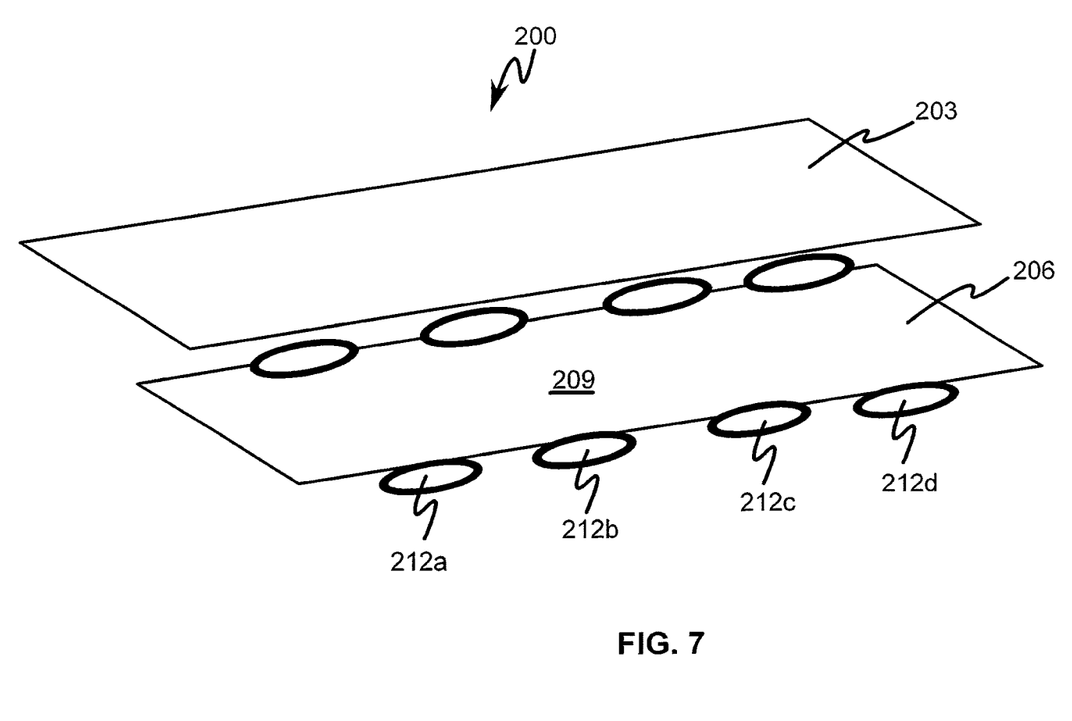
FIG. 7 is a schematic view of another alternate embodiment of the invention.
Figure 8:
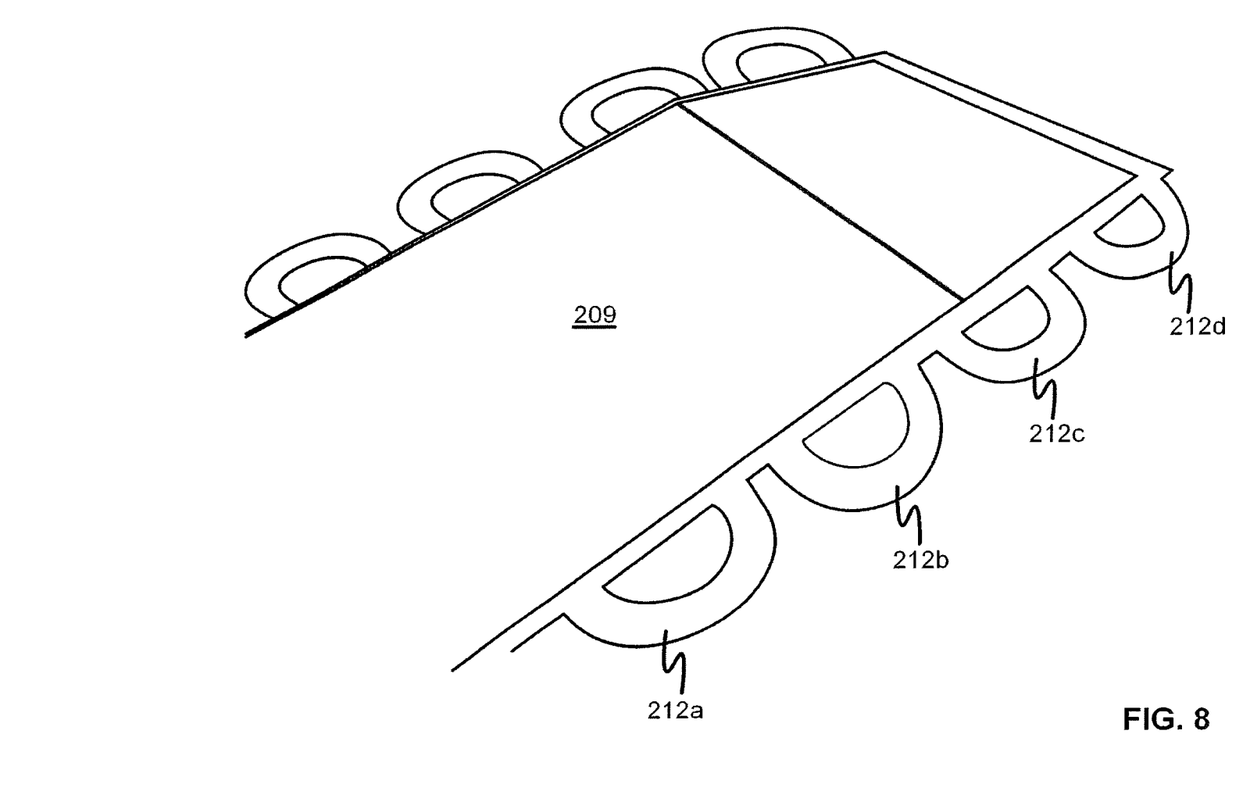
FIG. 8 is a perspective view of a subassembly of the pad system shown in FIG. 7.

In FIG. 7, in another embodiment of the invention, a non-disposable pad assembly 200 may be constructed of two major components: a disposable pad subassembly 203 and a lower support structure 206 that may be cleaned for repeated use. The disposable pad subassembly 203 may be constructed of a standard viscoelastic pad that may be fused with an upper support structure. The upper support structure may be provided with an FDA approved adhesive or a similar bonding strength pressure sensitive adhesive (PSA) on its bottom surface for removably attaching the pad subassembly 203 to the lower support structure 206.

The lower support structure 206 has an upper surface 209 and a lower surface (not shown). The lower support structure 206 receives the pad subassembly 203 on the upper surface 209 and the lower surface of the lower support structure 206 rests on the surgical table 127 (FIG. 5). The lower surface may be provided with an anti-skid rubber foam strip and a pressure sensitive adhesive (PSA) strip for holding the pad subassembly in position on the surgical table 127. The lower support structure 206 may be provided with multiple handles 212a-d that provide a grabbing point for lifting the patient for transfer from one position to another position on the surgical table.

The lower support structure 206 may be formed from an FDA approved and cleanable woven fabric material. The internal structure of the disposable pad subassembly 203 may include both viscoelastic and a compressible/expandable foam fused with a dense and compressible foam support structure. This combination prevents sagging or bunching of the materials with respect to the patient during a lifting scenario. The lower structure 206 may be enclosed via a cleanable fabric. As described above a heating element may be incorporated into the design which allows the device to be a modular patient warming and positioning device. Current under body warming mattress top systems are not modular, do not contain handles, and force providers to place the patient in a less than optimal position.

The present invention contemplates that many changes and modifications may be made. Therefore, while the presently-preferred form of the emissions measuring system has been shown and described, and several modifications and alternatives discussed, persons skilled in this art will readily appreciate that various additional changes and modifications may be made without departing from the spirit of the invention, as defined and differentiated by the following claims.

The invention claimed is:

1. An apparatus for positioning a patient in a gravity dependent surgical position on a surgical table, the apparatus comprising:
 a base having a top surface and a bottom surface, the bottom surface having a strip of pressure sensitive adhesive (PSA) and one or more foam strips disposed along the periphery of the bottom surface disposed thereon for inhibiting movement of the bottom surface relative to the table when the table is placed in the gravity dependent surgical position;
 a high friction coefficient foam pad supported above the base;
 a reinforcing layer disposed between the high friction coefficient foam pad and the base;

a plurality of handles configured and arranged such that each handle is attached to one at the base, the high friction coefficient foam pad and the reinforcing layer;

wherein the base, high friction coefficient foam pad, and reinforcing layer are connected provide a reinforced pad assembly that is configured to prevent bunching when lifting or repositioning the patient during surgical table positioning changes required during surgery, the reinforced pad assembly configured for movement in multiple directions during surgery;

wherein the pressure sensitive adhesive and the one or more foam strips on the bottom surface of the base releases contact with the surgical table easier than pressure sensitive adhesive alone when the patient is lifted via the handles to allow minimal lifting by a user to reduce overall load as compared to use of draw sheets and by hand, and then the base reattaches to the surgical table winch keeps the apparatus in place during gravity dependent surgical table positions used during surgery;

wherein the base, high friction coefficient foam pad, reinforcing layer and plurality of handles are connected to form a unitary disposable combination.

2. The apparatus of claim 1, wherein the base further comprises a nonwoven material.

3. The apparatus of claim 1, wherein the base further comprises an SMS (spun-melt-spun) material.

4. The apparatus of claim 1, wherein the base further comprises a celluloid material.

5. The apparatus of claim 1, further comprising a warming support structure inlay.

6. The apparatus of claim 1, wherein the reinforcing layer is foam configured to prevent laxity of the pad and bunching when lifting a patient.

7. The apparatus of claim 1, wherein the reinforcing layer is cardboard.

8. The apparatus of claim 5, wherein the warming support structure is placed between nonwoven materials.

* * * * *